US007404807B2

(12) United States Patent
Callaway

(10) Patent No.: US 7,404,807 B2

(45) Date of Patent: Jul. 29, 2008

(54) PEDIATRIC NASAL GASTRIC VENT TUBE

(76) Inventor: James Josiah Callaway, 615 Woodleigh Dr., Nashville, TN (US) 37215

(*) Notice: Subject to any disclaimer, the term of this patent is extended or adjusted under 35 U.S.C. 154(b) by 0 days.

(21) Appl. No.: 11/723,083

(22) Filed: Mar. 16, 2007

(65) Prior Publication Data

US 2007/0219485 A1 Sep. 20, 2007

Related U.S. Application Data

(60) Provisional application No. 60/783,156, filed on Mar. 17, 2006.

(51) Int. Cl.
*A61M 3/00* (2006.01)

(52) U.S. Cl. .......................... 604/45; 604/30; 604/324; 95/45

(58) Field of Classification Search .................. 604/45, 604/30, 324; 95/45
See application file for complete search history.

(56) References Cited

U.S. PATENT DOCUMENTS

| | | | | | |
|---|---|---|---|---|---|
| 4,239,793 | A | * | 12/1980 | Matsuura et al. | 428/216 |
| 4,725,268 | A | * | 2/1988 | Ostensen et al. | 604/323 |
| 5,252,222 | A | * | 10/1993 | Matkovich et al. | 210/650 |
| 5,374,243 | A | * | 12/1994 | Whalen et al. | 604/23 |
| 5,460,603 | A | * | 10/1995 | DeSantis | 604/30 |
| 2006/0231487 | A1 | * | 10/2006 | Bartley et al. | 210/506 |

* cited by examiner

*Primary Examiner*—Sam Chuan Yao
*Assistant Examiner*—Shefali D Patel
(74) *Attorney, Agent, or Firm*—Jacobson Holman PLLC

(57) ABSTRACT

To alleviate the spillage of formula from a nasal-gastric tube, a small (5 cc size) constant diameter barrel having a side arm is inserted into the N-G tube. The equal sized open ends of the barrel are closed with a membrane that allows air to pass through but is impervious to liquids. The barrel is made of clear nylon material approved by the FDA for contact with formula for the baby.

18 Claims, 3 Drawing Sheets

PEDIATRIC NASAL GASTRIC VENT TUBE

This is a complete application of provisional patent application Ser. No. 60/783,156, filed Mar. 17, 2006, hereby incorporated in its entirety by reference.

FIELD OF THE INVENTION

The present invention relates to the field of a vent for pediatric nasal gastric feeding tubes.

BACKGROUND OF THE INVENTION

A new born baby, especially those born pre-maturely, often require nutritional formula administered by a nasal-gastric (N-G) tube extending through the nose of the baby to its stomach. During feeding and/or as the result of digestive processes, air or gas accumulates in the baby's stomach. The air along with the gas of digestion of the tube feeding is preferably vented, rather than being allowed to pass through the gastro-intestinal tract. The venting of the gas benefits the baby by eliminating uncomfortable and sometimes painful accumulation of gas.

If the N-G tube is not "plugged" tightly at the end of the tube extending from the nasal passage, both air and formula can be expelled from the stomach and flow outwardly from the tube. This requires the nurse to plug the exit end of the tube with the tip of a barrel of a small syringe (3-5 cc), for example. Cotton or a gauze sponge is then inserted into the barrel of the syringe to allow gas to escape, along with some formula, from the barrel of the syringe. The regurgitated formula saturates the cotton or gauze and spills out onto the baby, baby's bed or bed linen. The spillage is messy and must be cleaned requiring additional effort on the part of the nursing staff.

SUMMARY OF THE INVENTION

To alleviate the spillage of formula from a nasal-gastric tube, a small (5 cc size) constant diameter barrel having a side arm is inserted into the N-G tube. The equal sized open ends of the barrel are closed with a membrane that allows air to pass through but is impervious to liquids. The barrel is made of clear nylon material approved by the FDA for contact with formula for the baby.

The pediatric nasal gastric vent tube of the present invention prevents spillage of formula while allowing gas to escape. A side arm of the vent tube is inserted into the feeding tube. Administered formula, when regurgitated is retained in the hollow body of the vent tube. Thus gas can escape through the membrane which is impervious to liquids, particularly baby formula. The membrane is a 3.0 micron oleophobic expanded polytetrafluorethylene (PTFE) membrane, such as TEFLON, on a nonwoven plain polyethylene terephthlate (PET) backing, such as is available from DuPont as a DACRON polyester fiber. Pressure sensitive acrylic adhesive around an edge of the membrane secures the membrane in place in the barrel.

The vent tube is a plastic cylinder barrel with a volume of 5 cc. The connector tube or side arm projects from a center of a side of the barrel. The connector tube permits the attachment of the vent tube to the gastric tube. Each of the two open ends of the vent tube is covered with a membrane.

Irrespective of the orientation of the plastic barrel there will be one membrane or membrane surface free of formula which allows gas to escape. Only if the barrel becomes full of formula where no gas can escape, the attendant drains formula back into the stomach, clearing at least one membrane. The vent tube is for single use and it is recommended that it be changed every 24 hours.

Accordingly, it is an object of the present invention to provide a pediatric nasal gastric vent tube in communication with a gastric feeding tube to alleviate gas pressure for a newborn baby.

It is another object of the present invention to provide a pediatric nasal gastric vent tube in communication with a gastric feeding tube to alleviate gas pressure for a newborn baby, with the vent tube including a cylindrical barrel having two open ends and the open ends being sealed with a gas permeable, liquid impermeable membrane.

It is still yet another object of the present invention to provide a pediatric nasal gastric vent tube in communication with a gastric feeding tube to alleviate gas pressure for a newborn baby, with the vent tube including a cylindrical barrel having two open ends and the open ends being sealed with a gas permeable, liquid impermeable membrane to allow gas to escape while retaining liquid, particularly baby formula, within the vent tube in an orientation having one end of the cylindrical barrel upright to allow escape of gas.

These and other objects of the invention, as well as many of the intended advantages thereof, will become more readily apparent when reference is made to the following description taken in conjunction with the accompanying drawings.

BRIEF DESCRIPTION OF THE DRAWINGS

The following drawings illustrate examples of various components of the pediatric nasal gastric vent tube disclosed herein, and are for illustrative purposes only. Other embodiments that are substantially similar can use other components that have a different appearance.

DETAILED DESCRIPTION OF THE PREFERRED EMBODIMENT

Figure 1:
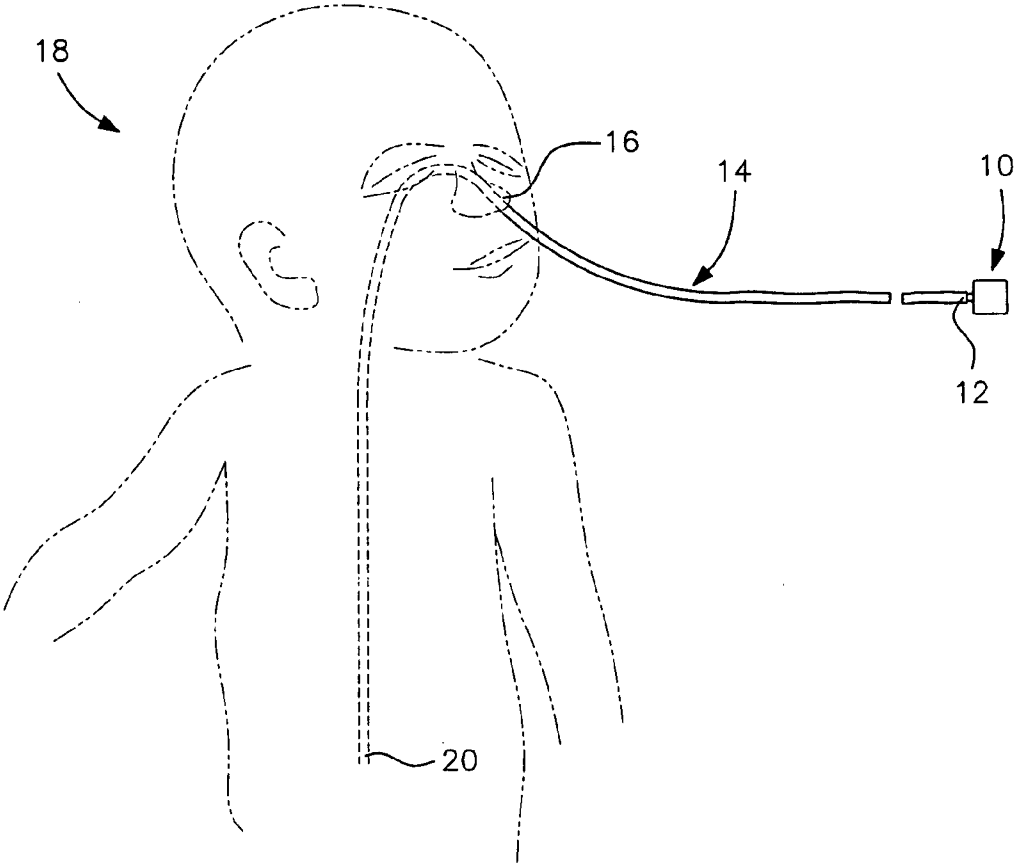
FIG. 1 is a schematic illustration of the pediatric nasal gastric vent tube according to the present invention secured to a gastric feeding tube for a newborn baby.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2:
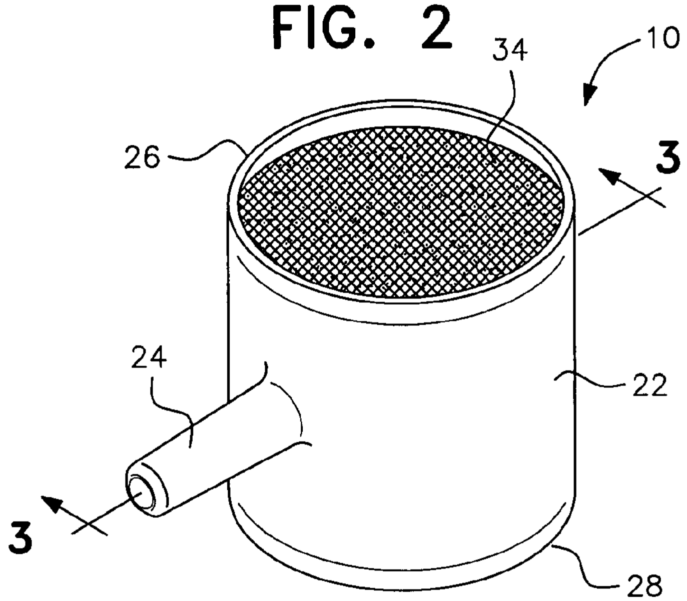
FIG. 2 is an enlarged perspective view of the pediatric nasal gastric vent tube of the present invention.
Figure 3:
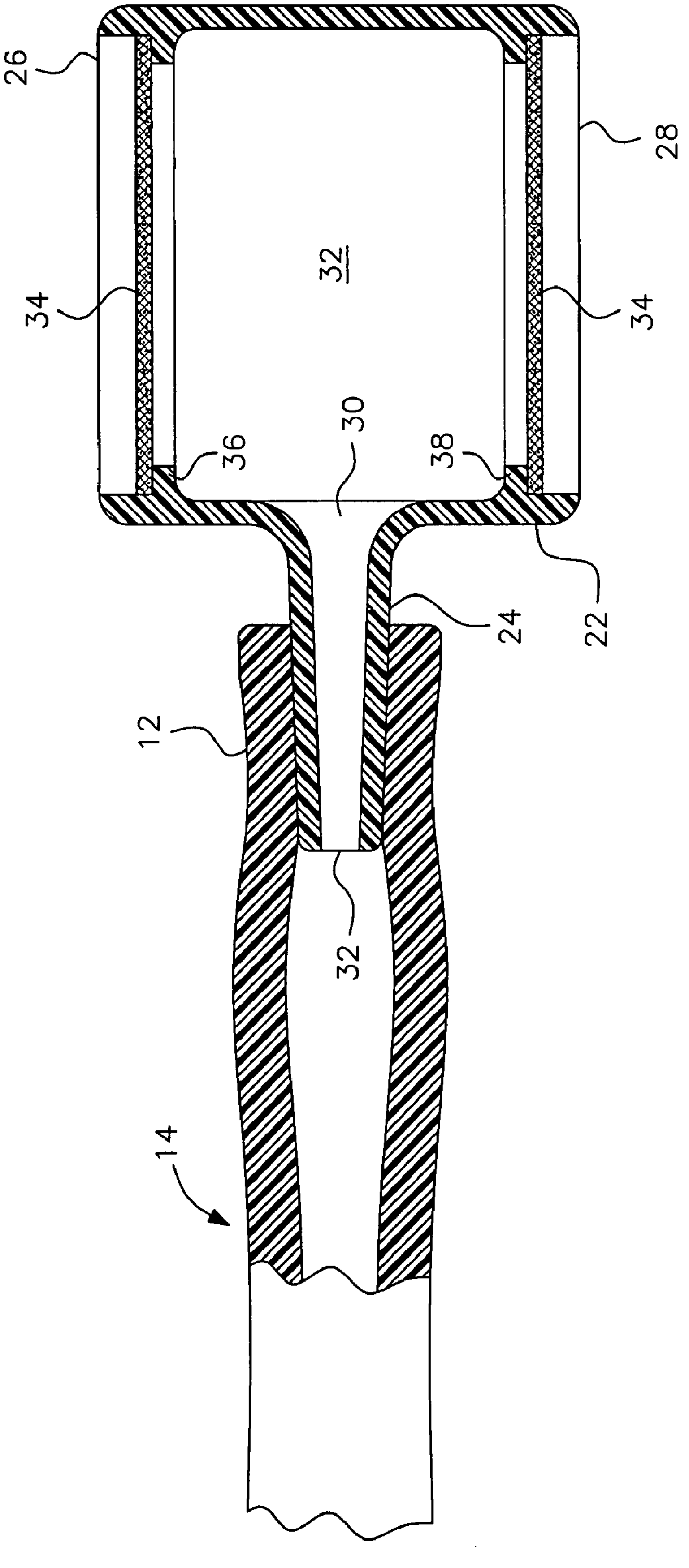
FIG. 3 is a sectional view of the pediatric nasal gastric vent tube taken along line 3-3 of FIG. 2 and shown connected to a gastric feeding tube.
Figure 4:
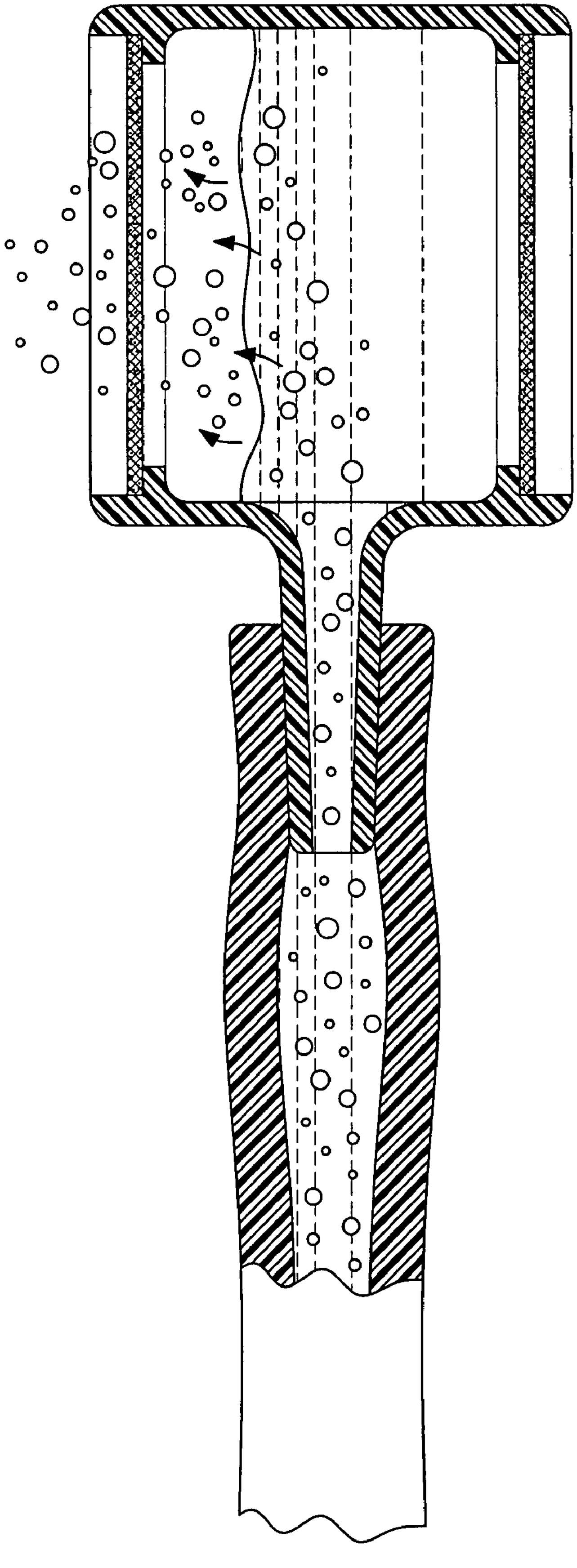
FIG. 4 is a sectional view of the pediatric nasal gastric vent tube shown in use allowing escape of gas while retaining liquid formula.

With reference to the drawings in general and to FIGS. 1 through 3 in particular, a pediatric nasal gastric vent tube embodying the teachings of the present invention is generally designated as 10. With reference to its orientation in FIG. 1, the vent tube 10 is located at one end 12 of a gastric feeding tube 14. The gastric feeding tube 14 is passed through the nasal passage 16 of a baby 18 so as to communicate with the stomach of the baby at the opposite end 20 of the feeding tube 14. Feeding by the tube 14 is usually performed with premature babies. A more detailed explanation of the vent tube 10 will be made with reference to FIGS. 2 through 4.

In FIG. 2, the vent tube 10 is shown formed of a cylindrical hollow body 22, having a laterally projecting connector tube 24. The connector tube 24 is located midway between the opposite ends 26, 28 on a sidewall of the cylindrical barrel 22. Connector tube 24 is hollow having one end 30 communicating with the hollow interior 32 of the cylindrical barrel 22. The opposite, free end 32 is used for communication with end 12 of feeding tube 14.

Both of the open ends 26 and 28 of the cylindrical barrel 22 are sealed by an identical membrane 34. As best shown in FIG. 3, membranes 34 extend completely across the openings 26, 28. The membranes 34 are located on an internal circumferential projection 36 at end 26 and projection 38 at end 28. The projections 36, 38 form a recessed step for engagement by a pressure sensitive acrylic adhesive located on a peripheral edge of the membranes 34. The membranes 34 are thereby sealed in place.

In operation, the connected tube 24 is secured by a friction fit in end 12 of feeding tube 14. The cylindrical barrel 22 is positioned so that one of the openings 26, 28 sealed by a membrane 34 is in an upright, vertical orientation. In the event that the baby regurgitates formula previously fed to it, the formula passes through the feeding tube 14 and via connector tube 24 into the interior 32 of the cylindrical barrel 22. The liquid, by gravity, flows to the lower membrane in FIG. 4 at opening 28, and any gas released from the stomach is allowed to pass upwardly through the membrane 34 of opening 26.

The pediatric nasal gastric vent tube of the present invention allows passage of gas through either membrane 34 in the absence of fluid. However, if fluid should block one end of the cylindrical barrel 22, the opposite end is free to allow passage of gas and relieve discomfort of the baby.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A pediatric nasal gastric vent tube connected at a terminal end of a gastric feeding tube, the pediatric nasal gastric vent tube comprising a hollow barrel having two open opposite ends, a sidewall of the hollow barrel extending between the two open ends, a membrane extending across both of the two open ends of the hollow barrel, and a single connector tube extending from the hollow barrel for connecting the hollow barrel with the terminal end of the gastric feeding tube, the connector tube being located extending from the sidewall of the hollow barrel and between the two open opposite ends, the hollow barrel consisting of only three external openings, one opening each defined by the two open ends and the third opening at the single connector tube.

2. The pediatric nasal gastric vent tube as claimed in claim 1, wherein the membrane allows gas to pass through and is impervious to liquids.

3. The pediatric nasal gastric vent tube as claimed in claim 2, wherein the membrane includes two layers.

4. The pediatric nasal gastric vent tube as claimed in claim 3, wherein one of two layers is PTFE.

5. The pediatric nasal gastric vent tube as claimed in claim 4, wherein the other of the two layers is a nonwoven backing of the one layer.

6. The pediatric nasal gastric vent tube as claimed in claim 1, wherein the barrel is cylindrical.

7. The pediatric nasal gastric vent tube as claimed in claim 1, wherein the connector tube projects from a center of the sidewall of the barrel.

8. The pediatric nasal gastric vent tube as claimed in claim 1, wherein the membrane is three microns thick.

9. The pediatric nasal gastric vent tube as claimed in claim 1, wherein the barrel is disposable.

10. A pediatric nasal gastric vent tube comprising a barrel having two ends, the two ends being open, a membrane extending across both of the two open ends of the barrel, and a single hollow connector tube having two ends, the connector tube extending from the barrel at one end and terminating in a free end at the other end for communicating between the barrel and a gastric feeding tube, the barrel consisting of only three external openings, one opening each defined by the two open ends and the third opening at the free end of the single connector tube.

11. The pediatric nasal gastric vent tube as claimed in claim 10, wherein the membrane allows gas to pass through and is impervious to liquids.

12. The pediatric nasal gastric vent tube as claimed in claim 11, wherein the membrane includes two layers.

13. The pediatric nasal gastric vent tube as claimed in claim 12, wherein one of two layers is PTFE.

14. The pediatric nasal gastric vent tube as claimed in claim 13, wherein the other of the two layers is a nonwoven backing of the one layer.

15. The pediatric nasal gastric vent tube as claimed in claim 10, wherein the barrel is cylindrical.

16. The pediatric nasal gastric vent tube as claimed in claim 10, wherein the connector tube projects from a center of a sidewall of the barrel.

17. The pediatric nasal gastric vent tube as claimed in claim 10, wherein the membrane is three microns thick.

18. The pediatric nasal gastric vent tube as claimed in claim 10, wherein the barrel is disposable.

* * * * *